United States Patent [19]

Hinson

[11] Patent Number: 5,145,679
[45] Date of Patent: Sep. 8, 1992

[54] TOPICAL EMOLLIENT FOR PREVENTION AND TREATMENT OF CIRCULATORY INDUCED LESIONS

[76] Inventor: Joan B. Hinson, 2145 Third Creek Church Rd., Cleveland, N.C. 27013

[21] Appl. No.: 594,286

[22] Filed: Oct. 9, 1990

Related U.S. Application Data

[63] Continuation-in-part of Ser. No. 417,239, Oct. 5, 1989, abandoned.

[51] Int. Cl.⁵ .................. A61K 9/06; A61K 31/70; A61K 37/26; A61K 31/715
[52] U.S. Cl. .................. 424/401; 424/DIG. 13; 424/445; 424/556; 514/887; 514/925; 514/969; 514/873
[58] Field of Search ............... 424/DIG. 13, 401, 445, 424/556; 514/925, 3, 928, 969, 873, 887, 23

[56] References Cited

U.S. PATENT DOCUMENTS

| | | | |
|---|---|---|---|
| 4,414,202 | 11/1983 | Silvetti | 424/648 |
| 4,847,083 | 7/1989 | Clark | 424/680 |
| 4,885,163 | 12/1989 | Shaar et al. | 514/2 |
| 4,886,786 | 12/1989 | Lindstrom et al. | 514/2 |
| 4,889,844 | 12/1989 | Silvetti, Sr. et al. | 424/DIG. 13 |
| 4,983,581 | 1/1991 | Antoniades et al. | 514/12 |

*Primary Examiner*—Thurman K. Page
*Assistant Examiner*—James M. Spear
*Attorney, Agent, or Firm*—Bailey & Hardaway

[57] ABSTRACT

A topical emollient for the treatment of circulation induced lesions comprises a source of glucose and insulin. The topical emollient is utilized in a process wherein the emollient is applied to the affected surface for nourishment thereof and promotion of healing. The emollient also enhances the therapeutic benefits of other medicinal drugs which may be topically applied in conjunction with the insulin and glucose mixture.

5 Claims, No Drawings

TOPICAL EMOLLIENT FOR PREVENTION AND TREATMENT OF CIRCULATORY INDUCED LESIONS

CROSS REFERENCE TO RELATED APPLICATIONS

This application is a continuation-in-part of application Ser. No. 07/417,239 filed Oct. 5, 1989 abandoned.

BACKGROUND OF THE INVENTION

This invention relates generally to the art of medicine and more particularly to the art of treatment of skin lesions, skin ulcers, and other skin maladies, and the treatment of some circulatory disorders, and as a delivery device for transporting topically applied drugs through intact skin.

It has been known for many years that patients suffering from diabetes, phlebitis, or other circulatory problems often develop lesions or ulcers which are difficult to treat. The affected tissue is often poorly nourished or has impaired circulation and the resulting lesions may heal slowly if at all. Further, many diabetic patients suffer from neuropathy which predisposes the patients to falls and subsequent injuries which are slow to heal and subject to secondary infections. Infected areas which fail to respond to traditional treatment protocols often become gangrenous and require amputation of the affected limb.

The treatment for such maladies has involved two general strategies; One, an attempt to increase circulation to the affected tissue and secondly, to treat the lesions by the use of general antibiotics to prevent infection. For diabetic patients in particular, insulin packs and insulin/transferrin packs have been used in the treatment of diabetic gangrene. However, all of these methods have had only limited success.

One difficulty in the treatment protocol is that many useful medicines to treat skin circulatory disorders require oral, subcutaneous or other delivery systems because the biologically active molecules are unable to be effectively absorbed or utilized through the skin. To date, transport of many medicines is unable to occur through the skin surface. Therefore, much room for improvement exists in the art.

SUMMARY OF THE INVENTION

It is thus an object of this invention to provide a novel topical emollient which when applied to circulatory induced lesions promotes nourishment of the affected cells, thereby eliminating the source of the lesions.

It is a further object of this invention to provide a novel process for the treatment of circulatory induced lesions.

It is a further object of this invention to provide a novel emollient which facilitates the uptake of biologically active molecules across the skin's surface.

It is a still further object of this invention to provide a process where topically applied medications can be more effectively utilized by the target tissues.

These as well as other objects are accomplished by a topical emollient comprising of a combination of glucose and insulin. The topical emollient is utilized in a process wherein the mixture is applied to the affected surface for nourishment thereof and promotion of healing.

DETAILED DESCRIPTION

In accordance with this invention it has been surprisingly found that a source of glucose and insulin, applied to a lesion, promoted the healing of the affected surface. This is surprising since it has here-to-fore been felt that insulin would not pass through the skin surface. However, in accordance with this invention, it has been found that when applied with a source of glucose, the insulin mixture provides or stimulates nourishment to the affected area. Further, it has been found that the aqueous glucose and insulin mixture enhances the therapeutic benefits of other topically applied medications.

By way of example, topical applications of hydrocortisone cream, when applied according to the claimed invention, show increased therapeutic benefits consistent with an enhanced uptake or more efficient utilization of the absorbed drug. As such, the claimed invention will enable faster healing and lower concentrations of drugs to be topically applied to affected areas. This will not only lower the cost of treatment but may significantly reduce undesirable drug side effects. As the effective drug concentration is lowered, dose-responsive side effects will be lessened. In addition, drugs which may not ordinarily be administered through the skin may become candidates for topical administration via the claimed process.

The critical minimum concentrations and ratios of glucose and insulin for effective treatment have not been determined. An effective insulin concentration, however, is believed to be as low as 0.06 units/ml in a 2% glucose solution. Effective treatment has been obtained with concentrations of insulin ranging from 0.06 units/ml to 2.0 units/ml. Similarly, glucose concentrations ranging from 2% to the highly concentrated levels found in strained honey, have all been successfully used.

It is likely that all the effective doses to date contained an excess concentration of both insulin and glucose. Since the insulin/glucose mixture is extremely safe as topically applied and relatively inexpensive, the critical lower limit of activity has not been determined. In addition, the minimum effective concentrations of the claimed invention may vary widely depending upon the age, general health, and the surface integrity of the patient's skin.

The insulin/glucose emollient is kept cool and away from strong light. Under these conditions, it has been found that the emollient remains stable and effective for at least several weeks. The emollient is topically applied to the affected area by gloved hand on intact skin, keeping the skin moist for at least 10 minutes and using a sterile gauze pad to apply the solution to broken skin areas to keep affected area moist for at least 10 minutes. Following the emollient, other topical medications may be applied to the affected surface. However, if desired, it would be possible to combine the emollient with other medication for a one-step application process.

The preferred insulin source is a mixture of 70% NPH insulin and 30% regular insulin. This ratio provides both long duration insulin (NPH) and a quicker response insulin (regular) though successful results have been obtained when both forms of insulin were used individually.

Having generally set forth the invention the following specific examples are given as an illustration thereof.

EXAMPLE 1

A male diabetic patient 53 years of age had open diabetic lesions on one foot and ankle consisting of multiple lesions having an area of one to one and one-half (1-1½) square inches in various stages of skin break down. The trial was conducted by applying three times a day a topical ointment of 0.6 units/ml of regular insulin in a 5% glucose solution. Within five days improvement of the patients condition had occurred. The patient was discharged from the hospital and instructed to continue the application of the mixture.

EXAMPLE 2

An elderly diabetic male patient was homebound because of diabetic neuropathy. The patient had a scalp ulcer approximately one and one-half (1½) inches in diameter. The patient had been treated about two (2) years with very little success. The scalp ulcer was treated with a mixture of 2.0 units/ml of NPH insulin in a strained honey solution. This mixture was applied once a day and within two (2) weeks the ulcer was healed.

EXAMPLE 3

A 61 year old female patient suffering with severe varicose veins and phlebitis was treated with a 0.4 units/ml of insulin (a combination of 70% NPH insulin and 30% regular insulin) in a 2% glucose solution. Prior to treatment the patient suffered almost constant pain even early in the morning. This had been a constant problem for thirty (30) years. The mixture was kept cool and away from light and was applied to the legs and feet three (3) times a day at meal time. After five (5) days of treatment the patient was free of pain in the feet and legs even at the end of the day. This was the first comfort that the patient had in some thirty (30) years. After fifteen (15) months there have been no symptoms of phlebitis and there has been a slow but constant reduction in the size of the varicosities.

EXAMPLE 4

A 38 year old female patient was suffering from a skin rash on her wrist. One half of the affected rash area was treated with a topical ointment of 0.5% hydrocortisone cream. The other half of the rash was treated with a mixture of 0.4 units/ml insulin (a combination of 70% NPH insulin and 30% regular insulin) and 2% glucose followed by an application of 0.5% hydrocortisone cream. A marked increase in the healing and recovery of the affected area was noted in the portion of the rash treated with the hydrocortisone/insulin/glucose mixture.

It is thus seen that the emollient and process of this invention provide a topical emollient which prevents and promotes healing of lesions and ulcers caused by circulatory problems and increases the effectiveness of other topical medicines applied in conjunction with the claimed invention. Many variations are apparent to those of skill in the art from a reading of the above description which is exemplary in nature. Such variations are embodied within the spirit and scope of this invention as measured by the following appended claims.

That which is claimed is:

1. A topical emollient for the treatment of skin lesions and disorders consisting essentially of:
   a mixture of an effective amount of a glucose solution containing insulin sufficient to treat skin disorders.

2. The emollient according to claim 1 wherein said source of glucose is honey.

3. A process for treating circulatory induced lesions comprising the steps of:
   applying to one of said lesions a mixture consisting essentially of a glucose solution containing insulin sufficient for treatment of said one of lesions.

4. A process for introducing a biologically active molecule across a surface of a patient's skin comprising the steps of:
   applying to said surface of said patient's skin a mixture containing a solution consisting essentially of glucose solution containing an effective amount of insulin, and a source of said biologically active drug.

5. A process for enhancing the therapeutic benefits of a biologically active compound comprising the steps of:
   applying said compound to a surface of a patient's skin, said compound being carried with a solution consisting essentially of a glucose solution containing insulin sufficient to enhance said therapeutic benefits.

* * * * *